(12) United States Patent
Legay et al.

(10) Patent No.: US 11,213,331 B2
(45) Date of Patent: Jan. 4, 2022

(54) MEDICAL IMPLANT FOR TARGETED INJECTION

(71) Applicant: INNOPROD MEDICAL, Toulouse (FR)

(72) Inventors: Philippe Alain Lucien Fernand Legay, Yville sur Seine (FR); Frédèric Deschamps, Paris (FR); Frédèric Peyre, Lasserre (FR)

(73) Assignee: INNOPROD MEDICAL, Plaisance-du-Touch (FR)

( * ) Notice: Subject to any disclaimer, the term of this patent is extended or adjusted under 35 U.S.C. 154(b) by 238 days.

(21) Appl. No.: 16/312,632

(22) PCT Filed: Jun. 20, 2017

(86) PCT No.: PCT/FR2017/000126
§ 371 (c)(1),
(2) Date: Dec. 21, 2018

(87) PCT Pub. No.: WO2017/220873
PCT Pub. Date: Dec. 28, 2017

(65) Prior Publication Data
US 2019/0209222 A1 Jul. 11, 2019

(30) Foreign Application Priority Data
Jun. 21, 2016 (FR) ..................................... 16/00992

(51) Int. Cl.
*A61B 17/70* (2006.01)
*A61B 17/84* (2006.01)
(Continued)

(52) U.S. Cl.
CPC ...... *A61B 17/8811* (2013.01); *A61B 17/7098* (2013.01); *A61B 17/84* (2013.01); *A61B 17/864* (2013.01); *A61B 17/8841* (2013.01)

(58) Field of Classification Search
CPC ............ A61B 17/7098; A61B 17/8625; A61B 17/863; A61B 17/864; F16B 31/021
See application file for complete search history.

(56) References Cited

U.S. PATENT DOCUMENTS 4,653,487 A * 3/1987 Maale ................ A61B 17/7098
606/62
5,941,885 A * 8/1999 Jackson ............. A61B 17/7076
606/104
(Continued)

FOREIGN PATENT DOCUMENTS

| EP | 1 110 510 A1 | 6/2001 |
|---|---|---|
| WO | 2011/063240 A1 | 5/2011 |
| WO | 2014/149746 A1 | 9/2014 |

OTHER PUBLICATIONS

International Search Report, dated Sep. 15, 2017, from corresponding PCT/FR2017/000126 application.

*Primary Examiner* — Nicholas W Woodall
(74) *Attorney, Agent, or Firm* — W & C IP

(57) ABSTRACT

Disclosed is an implant through which a liquid or pasty material can be injected in a targeted manner. This implant is composed of: a main implant with a lumen extending along its entire length, the body of the main implant being of hexagonal cross section, with the plane faces drilled with internally threaded holes which open into the lumen and are intended to remain open or to be plugged by one or more micro screws of the complementary implants, the distal end and proximal end of the implant being threaded; one or more complementary implants, for each of which the micro screw thereof, intended to cooperate with the internally threaded holes of the main implant, is connected to its insertion sleeve by way of a separable zone. The implant is intended in particular for surgical interventions.

8 Claims, 1 Drawing Sheet

(51) Int. Cl.
*A61B 17/86* (2006.01)
*A61B 17/88* (2006.01)

(56) References Cited

U.S. PATENT DOCUMENTS

| | | | |
|---|---|---|---|
| 7,261,716 B2 | 8/2007 | Strobel et al. | |
| 9,681,901 B2* | 6/2017 | Wolter | A61B 17/7283 |
| 2004/0068261 A1* | 4/2004 | Fourcault | A61B 17/863 |
| | | | 606/67 |
| 2007/0233123 A1* | 10/2007 | Ahmad | A61B 17/863 |
| | | | 606/307 |
| 2009/0248030 A1* | 10/2009 | Butler | A61B 17/7035 |
| | | | 606/104 |
| 2011/0040337 A1 | 2/2011 | Budassi | |
| 2011/0060373 A1 | 3/2011 | Russell et al. | |

\* cited by examiner

MEDICAL IMPLANT FOR TARGETED INJECTION

FIELD OF INVENTION

The present invention relates to a medical implant for the targeted injection of a liquid or pasty material into a bone cavity, thereby promoting filling and/or consolidation, without the risk of constraining any nerve, and/or any other soft part, which may be present near the injection site.

BACKGROUND OF INVENTION

The prior art proposes various materials used in osteosynthesis, nails and screws, cannulas so as to be guided during the installation. These different materials can be used to drive an acrylic cement, via the lumen, but in no case can target the site or sites of injection. The materials currently used by practitioners are not dedicated to this technique,
either do not allow to inject, thus obliging to carry out differentiated injections, by first practicing other ways, which means carrying out additional actions detrimental for the patient,
or do not mitigate the risk of touching the nerves or soft parts passing into the cavity, close to the implant, giving a risk of pain to the patient.

The present invention aims to provide the opportunity for the practitioner to solve these problems, through the use of a modular implant, which allows, thanks to a main implant and complementary implants, to meet the needs of the practice, and in particular to target areas, determined previously, which shall not receive any filler or consolidation.

This goal is achieved through a main implant, which may be a nail, a pin or a screw.

Advantageously, the implant described herein is an assembly composed of a bone screw intended to receive complementary implants, characterized:
in that said bone screw has three parts where the central part, called body, can be of cylindrical section, square or polygonal. Preferably, according to the invention, the section of the body of the bone screw is hexagonal so as to provide sufficient plane faces,
in that said hexagonal body comprises cylindrical holes passing right through it, as far as the longitudinal axis of the bone screw,
in that the cylindrical holes can be coated with a mechanical thread,
in that the longitudinal axis of the bone screw is hollowed out, so that the cylindrical holes open into this recess called lumen,
in that the proximal portion encloses a female cavity contiguous with an injection chamber that can extend over the entire length of the body of said screw that is to receive a specific cannula from a dedicated instrumentation,
in that said complementary implants are plugs, preferably micros screws, called to plug one, several, or all the threaded holes of the main implant,
in that said complementary implants are composed of two parts, the proximal part of which is a rod, called an insertion sleeve, and the distal part is a stopper, usefully a micro screw with a mechanical thread, as well as the tapping of the holes. cylindrical body of the main implant,
in that said micro screw is of thickness equal to the depth of each of the threaded holes of the body of the main screw,
in that the insertion sleeve and the distal micro screw are separated by a breakable zone,
in that the insertion sleeve, for positioning the micro screw, detaches in shear, or bending, at the breakable zone, at the end of clamping.

The bone screw has a thread at each end, said threads being of different pitch. Advantageously, the proximal thread may be narrower than the distal thread so as to perform a slight compressive tightening.

The insertion sleeve of each complementary implant may be cylindrical or of square or polygonal section.

Advantageously, said insertion sleeve may comprise, at its end, a constricted and flat portion allowing a better grip for setting up and detaching the micro screw.

BRIEF DESCRIPTION OF THE DRAWINGS

The invention will be better understood and other features and advantages thereof will become apparent with reference to the accompanying diagrammatic drawings, showing, by way of non-limiting example, an embodiment of the targeted injection implant which it concerns.

DETAILED DESCRIPTION

Figures 1, 2, 3:
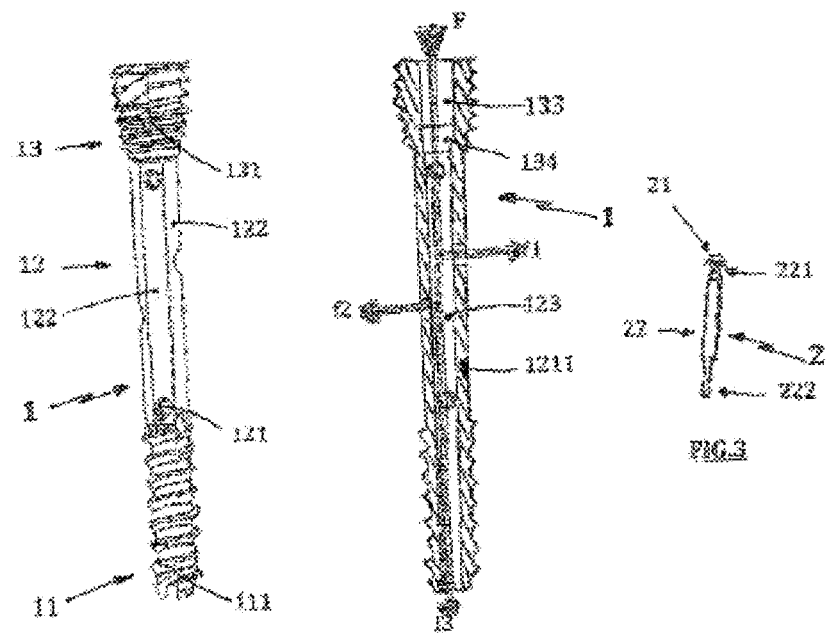
FIG. 1 represents a view of the main implant.
FIG. 2 is a longitudinal section of the main implant.
FIG. 3 represents a view of a complementary implant.

FIG. 1 represents a view of the main implant 1 comprising of a distal threaded portion 11, an intermediate body 12 and a proximal threaded portion 13, the assembly being integral. The intermediate body 12, hexagonal in section in a circle of the same diameter as the threaded portion 11, is perforated with a variable number, depending on its length, preferably threaded holes 121 on its flat faces 122. The distal threaded portion 11 and the proximal threaded portion 13 are provided with a self-piercing and self-tapping principle, respectively 11 and 131.

FIG. 2 is a longitudinal section of the main implant 1, having a recess 123, called a lumen, communicating with the tapped holes 121, in order to channel the conduction of a liquid or slurry material, injected at the chamber of FIG. injection 134, which may extend over the entire length of the body of said screw, contiguous to the cavity 133 called to cooperate with a positioning tool, outside the main implant 1. The arrow F shows the path of the liquid or pasty material in the lumen 123 and, for example, its lateral outlets f1, f2, through the tapped holes 121 and the end of the lumen 123 represented by f3, as well as the blocking the same liquid or slurry material, stopped by the closure that operates a micro screw 21 cooperating with a threaded hole 121 in position 1211.

FIG. 3 shows the view of a complementary implant 2, composed of a plug, preferably a micro screw 21 adjacent to an insertion sleeve 22 via a breakable zone 221. Each of said microphones screws 21 is called to plug a threaded hole 121, previously determined, the body 12 of the main implant 1 to prevent the diffusion of liquid or slurry material at this precise location. Advantageously, the sleeve 22 may end with a recess 222 allowing a better grip to insert the micro screw 21 into the threaded holes 121 and disconnect it at the end of clamping.

Figure 4:
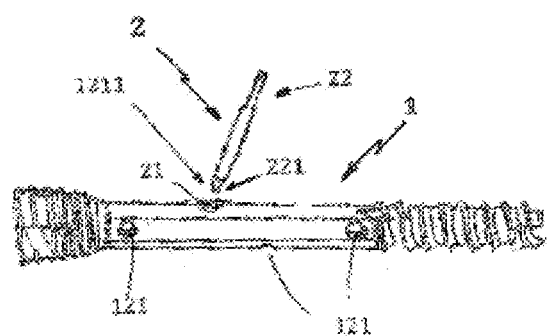
FIG. 4 represents a main implant, on which a complementary implant has been positioned, after rupture of the insertion sleeve.

FIG. 4 represents an embodiment of the invention composed of a main implant 1, a threaded hole 121 of which is plugged by the action of a micro screw 21, detached from its insertion sleeve 22, after rupture of the breakable zone 221, to stop the diffusion of the liquid or slurry material at a predetermined site, as shown, for example, in position 1211.

As can be seen from all the foregoing, the invention provides an implant, in particular an osteosynthesis implant, having, in comparison with homologous screws of the prior art or borrowed from other disciplines, the decisive advantage of making it possible to target the injecting a liquid or slurry material into a bone cavity, in particular to achieve filling or consolidation, under the best conditions, and avoiding any risk of constraining any nerve, and/or any other soft part, which may be present at near the injection site.

It goes without saying that the invention is not limited to the embodiment described above by way of example, but that it extends to all the equipment and all forms of embodiments covered by the claims herein—after annexed. While various embodiments have been described and illustrated, the detailed description is not to be construed as being limited hereto. Various modifications can be made to the embodiments by those skilled in the art without departing from the true spirit and scope of the disclosure as defined by the claims.

The invention claimed is:

1. A medical implant for targeted injection comprising:
a main implant; and
one or more complementary implants, each of the complementary implants including an insertion sleeve and a stopper shaped as a micro-screw,
wherein the main implant has three parts, the three parts of the main implant including
a central part of polygonal section, the central part having flat faces over its entire periphery, the flat faces being perforated up to a longitudinal axis of the central part and into lumen orifices, the lumen orifices being tapped holes, the tapped holes being configured to be plugged by one or more of the micro-screws from the one or more complementary implants, or to remain open, and
a proximal portion enclosing an injection chamber extending over an entire length of the central part of the main implant, the injection chamber being configured to receive a specific cannula-dedicated instrumentation,
wherein each of the micro-screws is configured to plug one of the tapped holes of the main implant, and is separated from one of the insertion sleeves by a breakable zone, wherein the insertion sleeve of the one or more complementary implants is configured to be terminated by a constriction, wherein the constriction is shaped as a singular flat protrusion at an end of the insertion sleeve having a reduced width as compared to a central portion of the insertion sleeve and is configured to allow a hand to grip the constriction to insert the micro-screw in one of the tapped holes and disconnect the micro-screw at an end of tightening.

2. The medical implant for targeted injection according to claim 1, wherein the micro-screws are configured to plug the tapped holes to stop diffusion of a material, liquid or slurry, in targeted and previously determined sites, as presented in position.

3. The medical implant for targeted injection according to claim 1, wherein the breakable zone is configured to separate the insertion sleeve, by shearing or bending, after screwing said micro-screw in the one of the tapped holes of the main implant.

4. The medical implant for targeted injection according to claim 1, wherein ends of the main implant are threaded portions, each of the threaded portions having a self-piercing and self-tapping principle.

5. The medical implant of claim 1, wherein the polygonal section of the body is hexagonal.

6. The medical implant for targeted injection according to claim 5, wherein the micro-screws are configured to plug the tapped holes to stop diffusion of a material, liquid or slurry, in targeted and previously determined sites, as presented in position.

7. The medical implant for targeted injection according to claim 5, wherein the breakable zone is configured to separate the insertion sleeve, by shearing or bending, after screwing said micro-screw in the one of the at least one tapped hole of the main implant.

8. The medical implant for targeted injection according to claim 5, wherein ends of the main implant are threaded portions, each of the threaded portions having a self-piercing and self-tapping principle.

* * * * *